US00PP16519P2

(12) United States Plant Patent
Trees

(10) Patent No.: US PP16,519 P2
(45) Date of Patent: May 9, 2006

(54) ***GERANIUM* PLANT NAMED 'BALCOLVIO'**

(50) Latin Name: *Pelargonium peltatum*
Varietal Denomination: Balcolvio

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 107 days.

(21) Appl. No.: 11/017,370

(22) Filed: Dec. 20, 2004

(51) Int. Cl.
*A01H 5/00* (2006.01)

(52) U.S. Cl. ..... Plt./332
(58) Field of Classification Search ..... Plt./332
See application file for complete search history.

(56) References Cited

U.S. PATENT DOCUMENTS

PP11,720 P * 12/2000 Trees ..... Plt./332
PP13,568 P2 * 2/2003 Trees ..... Plt./332

OTHER PUBLICATIONS

UPOV ROM GTITM Computer Database, GTI Jouve Retrieval Software 2005/02 Citations for 'Balcolvio'.*

* cited by examiner

*Primary Examiner*—Kent Bell
*Assistant Examiner*—W. C. Haas
(74) *Attorney, Agent, or Firm*—Wood, Phillips, Katz, Clark & Mortimer

(57) ABSTRACT

A new and distinct cultivar of *Geranium* plant named 'Balcovio' characterized by its semi-double red-purple-colored flowers, dark green-colored foliage, and vigorous, upright, and trailing growth habit.

2 Drawing Sheets

Latin name of genus and species of plant claimed: *Pelargonium peltatum.*
Variety denomination: 'Balcolvio'.

BACKGROUND OF THE INVENTION

The present invention relates to a new and distinct cultivar of *Geranium* plant botanically known as *Pelargonium peltatum* and hereinafter referred to by the cultivar name 'Balcolvio'.

The new cultivar originated as a single plant in a controlled breeding program in Arroyo Grande, Calif., during January 2000. The objective of the breeding program was the development of *Geranium* cultivars with a vigorous, upright and trailing growth habit, dark green-colored foliage, and new and unique flower color.

The female (seed) parent of the new cultivar was the proprietary *P. peltatum* breeding selection 2022, not patented, characterized by its semi-double, hot rose-colored flowers and dark green-colored ivy type foliage. The male (pollen) parent of the new cultivar was proprietary *P. peltatum* breeding selection BFP-1293, not patented, characterized by its semi-double, dark burgundy-colored flowers and dark green-colored ivy type foliage. The new *Geranium* was discovered and selected by the inventor as a single flowering plant within the progeny of the above stated cross-pollination during February 2001 at Arroyo Grande, Calif.

Asexual reproduction of the new cultivar by terminal stem cuttings since February 2001 at Arroyo Grande, Calif. and West Chicago, Ill., has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balcolvio' as a new and distinct cultivar of *Geranium* plant:

1. Semi-double red-purple-colored flowers.
2. Dark green-colored foliage.
3. Vigorous, upright, and trailing growth habit.

Plants of the new cultivar differ from plants of the female primarily in flower color and from plants of the male parent primarily in flower color.

Of the many commercially available *Geranium* cultivars known to the inventor, the most similar in comparison to the new cultivar is 'Balcolilac', U.S. Plant Pat. No. 11,720. However, in side by side comparisons, plants of the new cultivar differed from plants of 'Balcolilac' in the following characteristics:

1. Plants of the new cultivar exhibit darker flower color than plants of 'Balcolilac'.
2. Plants of the new cultivar are taller than plants of 'Balcolilac'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balcolvio'. The plants were grown for 12 weeks in a greenhouse at West Chicago, Ill.

DETAILED BOTANICAL DESCRIPTION

Figure 1:
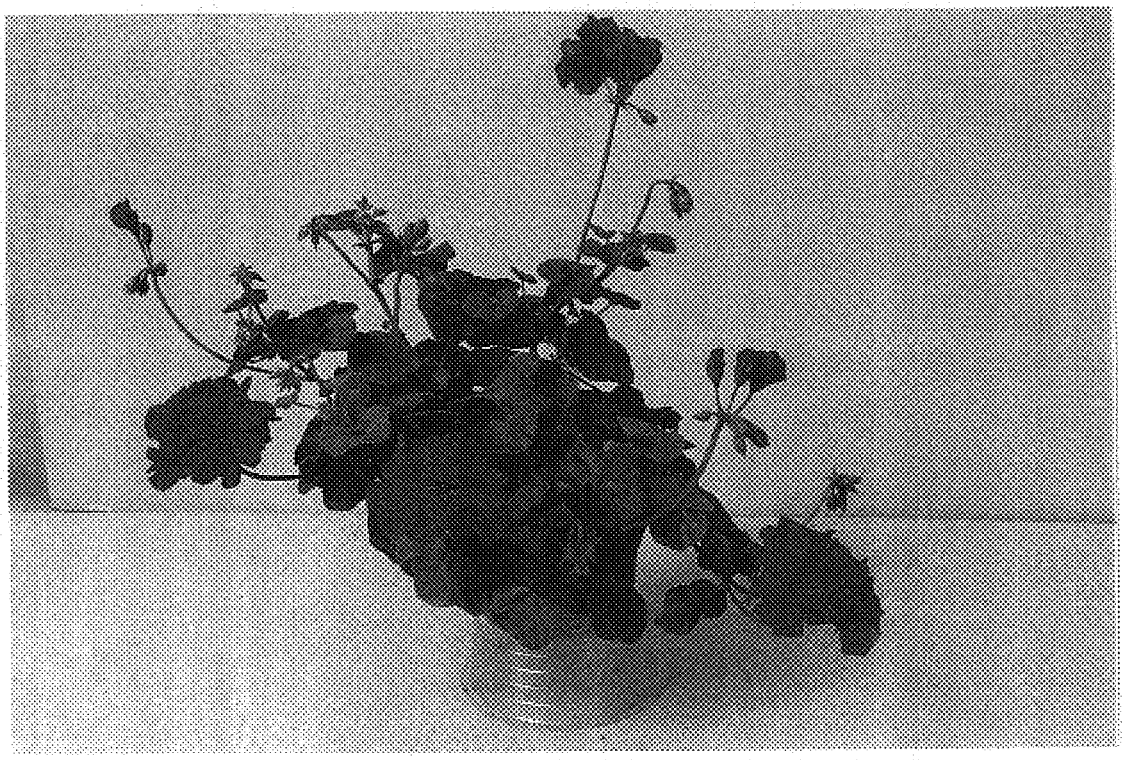
FIG. 1 illustrates a side view of the overall growth and flowering habit of 'Balcolvio'.
Figure 2:
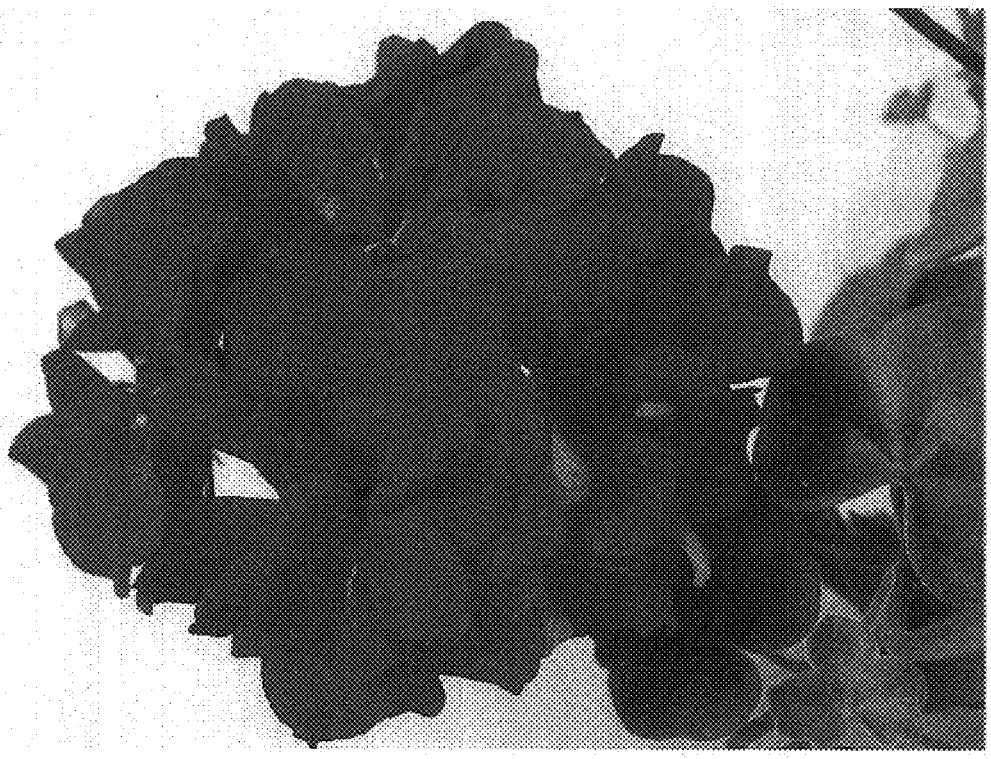
FIG. 2 illustrates a close-up view of a single umbel of 'Balcolvio'.
Figure 3:
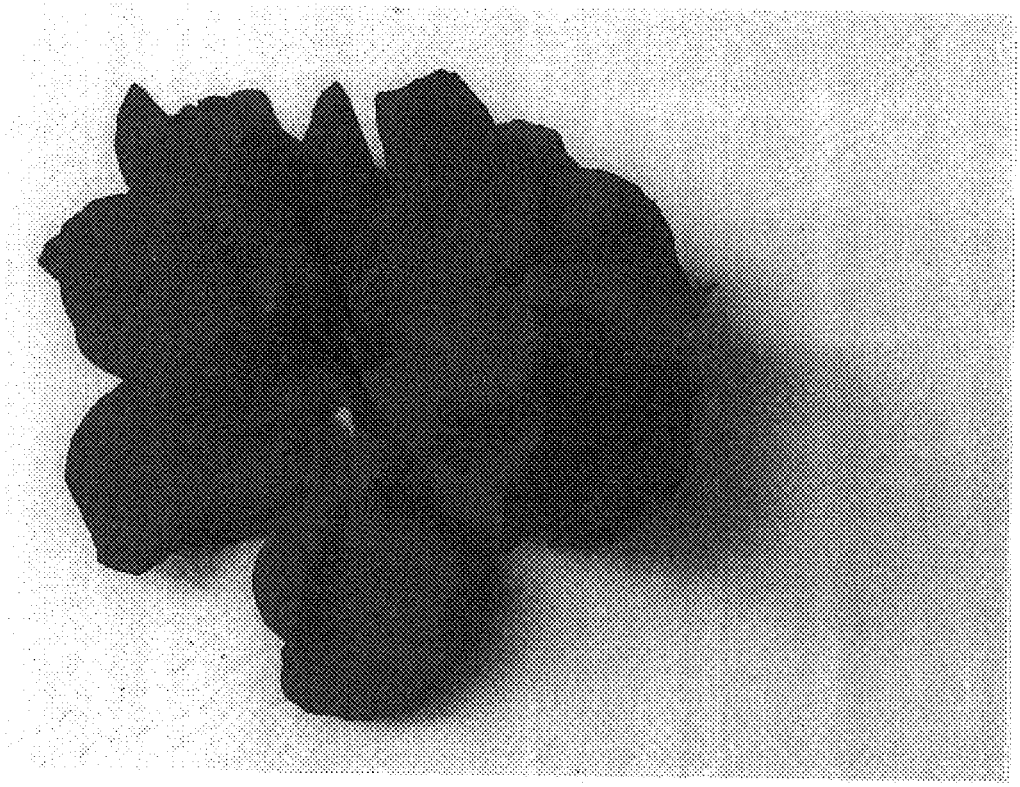
FIG. 3 illustrates a close-up view of a single flower of 'Balcolvio' showing the venation on the upper petals.
Figure 4:
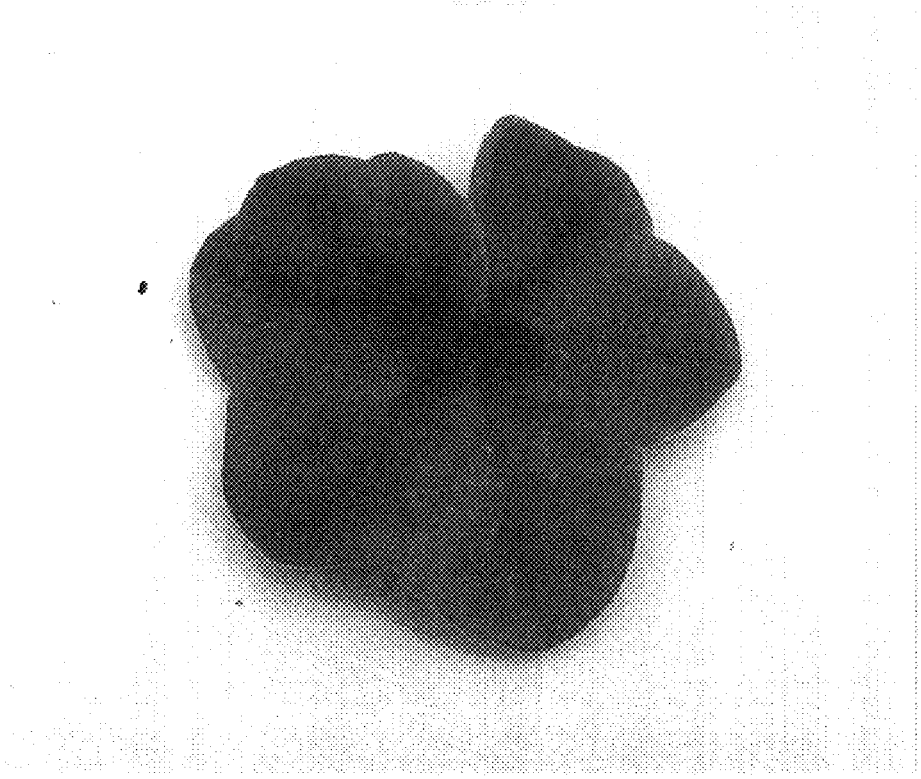
FIG. 4 illustrates a close-up view of a single leaf of 'Balcolvio'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Sep. 15, 2004 between 10:00 and 11:45 a.m. under natural light conditions, in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 9 weeks utilizing a soilless growth medium. Greenhouse temperatures were maintained at approximately 65° F. to 70° F. (18° C. to 21° C.) during the day and approximately 60° F. to 65° F. (15° C. to 18° C.) during the night. Greenhouse light levels of 4,000–6,000 footcandles were maintained during the day. Plants were pinched at three weeks after the planting of a rooted cutting.

Botanical classification: *Pelargonium peltatum* cultivar Balcolvio.

Parentage:

*Female parent.*—Proprietary *P. peltatum* breeding selection 2022, not patented.

*Male parent.*—Proprietary *P. peltatum* breeding selection BFP-1293, not patented.

Propagation:

*Type cutting.*—Terminal stem.

*Time to initiate roots.*—Approximately 10 to 14 days.

*Time to produce a rooted cutting.*—Approximately 21 to 28 days.

*Root description.*—Fibrous.

*Rooting habit.*—Freely branching.

Plant description:

*Crop time.*—Approximately 8 to 10 weeks from rooted cutting to finish.

*Growth habit and general appearance.*—Vigorous, upright, and trailing.

*Size.*—Height from soil level to top of plant plane: Approximately 22.8 cm. Width/area of spread: Approximately 31.4 cm.

*Branching habit.*—Freely basal branching. Approximately 2 main branches per plant.

*Branch.*—Length: Approximately 16.7 cm. Diameter: Approximately 3 mm. Texture: Dense, appressed. Color: 146A. Internode length at center of branch: Approximately 2.6 cm.

*Foliage.*—Number of leaves per lateral branch: Approximately 14. Form: Simple. Arrangement: Opposite. Shape: Peltate. Margin: Palmately lobed. Apex: Rounded. Base: Cordate. Venation pattern: Palmate. Texture of upper surface: Moderately pubescent. Texture of lower surface: Sparsely pubescent with moderate pubescence along veins. Color of upper surface of mature foliage: Closest to 146A with venation of 144A and zone of 200A around petiole attachment. Color of lower surface of mature foliage: 146B. Length of mature leaf: Approximately 3.7 cm. Width of mature leaf: Approximately 6.4 cm. Petiole length: Approximately 3.1 cm. Petiole diameter: Approximately 1.7 mm. Petiole texture: Densely pubescent on both upper and lower surface. Petiole color: 144A.

Flowering description:

*Flowering habit.*—'Balcolvio' is freely flowering under outdoor growing conditions with substantially continuous blooming from spring through autumn and year round under greenhouse conditions.

*Time to first flower.*—Approximately 8 weeks after planting of rooted cutting.

*Lastingness of individual bloom.*—Approximately 5 to 7 days.

Inflorescence description:

*Type.*—Hemispherical umbel. Position: Above foliage. Number of open umbels at any one time: 3. Number of developing umbels at any one time: 2. Umbel diameter: Approximately 8.5 cm. Umbel height/depth: Approximately 4.7 cm. Number of flowers per umbel: Approximately 7.

*Peduncle.*—Strong, erect. Length: Approximately 10.2 cm. Diameter: Approximately 2.9 mm. Texture: Densely pubescent. Color: 146A.

Flower description:

*Bud rate of opening.*—Generally takes 3 to 5 days for buds to progress from first color to fully open floret.

*Bud just before opening.*—Shape: Elliptic. Length: Approximately 1.6 cm. Diameter: Approximately 9 mm. Petal color: 63A. Sepal color: 144A.

*Corolla.*—Form: Semi-double. Shape: Round, slightly cupped. Diameter/width: Approximately 5.3 cm. Depth: Approximately 2.4 cm. Fragrance: None. Persistent.

*Petals/petaloids.*—Quantity: Approximately 14 petals and 3 petaloids per flower. Arrangement: Imbricate. Shape: Obovate. Apex: Obtuse. Base: Attenuate. Margin: Entire. Texture of upper and lower surface: Glabrous. Length of upper petal: Approximately 3.3 cm. Width of upper petal: Approximately 2 cm. Lower petal length: Approximately 2.5 cm. Lower petal width: Approximately 1.5 cm. Color of all petals and petaloids: Fully opened, upper surface: Closest to N66A and venation of 53A. Lower petals and petaloids are N155B at base. Color of all petals and petaloids: Fully opened, lower surface: N155D with venation of 46D.

*Pedicel.*—Strength: Strong. Angle: Acute. Length: Approximately 2.4 cm. Diameter: Approximately 1.4 mm. Texture: Densely pubescent. Color: Closest to 146A.

*Calyx/sepals.*—Quantity per flower: 5. Shape: Elliptic. Tip: Acuminate. Base: Truncate. Margin: Entire. Sepal length: Apprimately 1.5 cm. Width of largest sepal: 5 mm. Width of smallest sepal: 3 mm. Texture: Upper/inner surface: Glabrous. Lower/outer surface: Densely pubescent. Color: Upper and lower surface: 144A.

*Reproductive organs.*—Androecium: Stamen number: 8 per flower. Filament length: Approximately 5 mm. Filament color: 155C at base, N57C at tip. Anther length: Approximately 3 mm. Immature anther color:

15D. Mature anther color: Darker than 71A. Pollen amount: Moderate. Pollen color: 25A. Gynoecium: Pistil quantity: One per flower. Pistil length: Approximately 1.5 cm. Stigma shape: 5 pointed star. Stigma length: 5 mm. Stigma color: 61B. Style length: 2.5 mm. Style color: 13D. Ovary length: 7 mm. Ovary texture: Sericeous. Ovary color: 143B.

Seed and fruit production: Neither seed nor fruit production has been observed.

Disease and pest resistance: Resistance to pathogens and pests common to *Geraniums* has not been observed.

What is claimed is:

1. A new and distinct cultivar of *Geranium* plant named 'Balcolvio', substantially as herein shown and described.

* * * * *